United States Patent [19]

Rideout et al.

[11] 4,299,823

[45] Nov. 10, 1981

[54] PYRAZOLO PYRIMIDINE RIBOSIDE COMPOUNDS, PHARMACEUTICAL COMPOSITIONS AND METHOD OF USE

[75] Inventors: Janet L. Rideout, Raleigh; Thomas A. Krenitsky; Gertrude B. Elion, both of Chapel Hill, all of N.C.

[73] Assignee: Burroughs Wellcome Co., Research Triangle Park, N.C.

[21] Appl. No.: 159,240

[22] Filed: Jun. 13, 1980

[30] Foreign Application Priority Data

Jun. 14, 1979 [GB] United Kingdom ............... 20698/79

[51] Int. Cl.³ ....................... A61K 31/70; C07H 19/18
[52] U.S. Cl. ..................................... 424/180; 536/24; 536/26; 536/28; 544/262; 435/88; 435/92
[58] Field of Search ............................ 536/24, 26, 28; 424/180; 544/262

[56] References Cited

U.S. PATENT DOCUMENTS

| | | | |
|---|---|---|---|
| 3,074,929 | 1/1963 | Hitchings et al. | 536/26 |
| 3,074,930 | 1/1963 | Hitchings et al. | 536/26 |
| 3,269,917 | 8/1966 | Imada et al. | 536/24 |

FOREIGN PATENT DOCUMENTS 760283  12/1970  Belgium ............................ 544/262

*Primary Examiner*—Johnnie R. Brown
*Attorney, Agent, or Firm*—Donald Brown

[57] ABSTRACT

4-Substituted alkylthio-1-β-D-ribofuransylpyrazole-(3,4-d) pyrimidines are active against coccidia in vivo and unlike the 4-methylthio analogue, are non-toxic. Methods for preparing and using the compounds, intermediates in the preparation and compositions of the compounds are also described.

15 Claims, No Drawings

PYRAZOLO PYRIMIDINE RIBOSIDE COMPOUNDS, PHARMACEUTICAL COMPOSITIONS AND METHOD OF USE

The present invention relates to 4-(substituted)thio-1-β-D-ribofuranosylpyrazolo[3,4-d]pyrimidine derivatives which are useful as antiprotozoal agents, especially for treating or preventing coccidiosis.

Coccidiosis is caused by protozoa of the genus Eimeria, which infect susceptible hosts by contact with faeces of diseased animals. It is therefore particularly damaging when animals are kept in close contact, and is thus the most important disease of poultry. Various therapeutic and prophylactic agents are known for combatting coccidiosis and are used with differing degrees of success. These are usually administrated throughout the life of animals and there is consequently a risk of the protozoa developing resistance to one or more of these agents.

4-Methylthio-1-β-D-ribofuranosylpyrazolo[3,4-d]pyrimidine and close analogues were prepared as potential anticancer agents, (J-L.G. Montero, et al., J.Hetero Chem., 14, 483, (1977) R. P. Panzica, et al.; R. E. Harman, R. K. Robinsons and L. B. Towsend, (Eds.); Chemistry and Biology of Nucleosides and Nucleotides; Academic Press, New York; (1978), 121–134) but no other type of biological activity has been disclosed.

The 4-methylthiopyrazolo[3,4-d]pyrimidine riboside has now been tested against coccidia and whilst it has good in vitro activity, it was found to be highly toxic, causing unacceptable fatalities in chickens.

It has now been found that 4-(substituted)thiopyrazolo[3,4-d]pyrimidine ribosides, in which the substituent on the sulphur atom is a group larger than a methyl group, are also active against protozoa of the genus Eimeria. In contrast with the known 4-methylthio derivative, these compounds have surprisingly low toxicity towards the host animal and are therefore suitable for treating or preventing coccidiosis in poultry.

According to the present invention therefore there is provided a compound of formula (I)

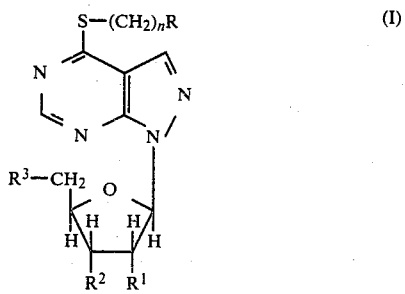

wherein n is an integer of 1 to 6 and R is a lower alkoxy or lower alkythio group or a phenoxy or phenylthio group or an unsubstituted or mono-substituted phenyl group, or, when n is 1 a group —C≡CR$^5$ wherein R$^5$ is a mono-, di-or tri-substituted phenyl or an unsubstituted phenyl, substituents for the aforementioned phenyl groups being selected from halogen atoms and lower alkyl, lower alkoxy, trifloromethyl, benzyloxy, phenoxy, amino, mono- or di-lower alkyl amino and hydroxyl groups, and either R$^1$, R$^2$ and R$^3$ are the same and are hydroxyl or acyloxy groups —O—CO—R$^4$ wherein R$^4$ is a hydrogen atom or a lower alkyl group or a substituted or unsubstituted phenyl group or R$^1$ and R$^2$ are hydroxyl or acyloxy groups as hereinbefore defined and R$^3$ is a phosphate group, or a salt thereof.

When R$^4$ is present as a phenyl group it may be optionally substituted with one or more of the substituents commonly known in the art and used as substituents for benzoyl esters of nucleosides and nucleotides, such as amino, hydroxyl, nitro, lower alkyl and lower alkoxyl groups and halogen atoms.

As used herein the terms "lower alkyl group" and "lower alkoxyl group" refer to such groups having from 1 to 4 carbon atoms.

If R$^4$ represents the salt of a phosphate group it is preferred that it is a pharmaceutically acceptable salt, such as the sodium or potassium salt in a mono or dibasic form. When R, in a compound of formula (I), is a phenyl group it is preferred that n has the value 1 to 3.

Compounds are particularly preferred when they embody two or more of the preferred features outlined above.

The most preferred compounds are the free ribosides, their phosphate esters and salts thereof.

Compounds of formula (I) may be prepared either by modification of the 4-substituent of a 1-B-D-ribofuranosylpyrazolo(3,4-d)pyrimidine (the precursor), or by linking the ribose moiety to a pyrazolo (3,4-d)pyrimidine derivative already bearing the correct atom or group at the 4-position.

According to a second aspect of the present invention there is therefore provided a process for producing compounds of formula (I) comprising either
  (a) The reaction between the precursor, a 4-(substituted)-1-β-D-ribofuranosylpyrazolo[3,4-d]pyrimidine derivative and a compound R(CH$_2$)$_n$X wherein n and R are as hereinbefore defined and either
    (i) X is a halogen atom and the 4-substituent of the precursor is a thio group and the reaction is performed in the presence of an organic or inorganic base or a basic resin in an aqueous, a lower alcoholic or an aprotic solvent; or
    (ii) X is an appropriate mercaptide radical and the 4-substituent of the percursor is a halogen atom or an alkylthio or aralkylthio group and the reaction is performed in the presence of an aprotic solvent; or
  (b) the reaction of a compound of formula (II)

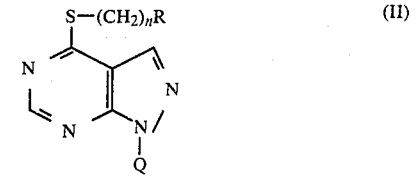

wherein R is as hereinbefore defined and Q is an appropriate leaving atom or group, with a riboside donor system by chemical, enzymatic or microbiological methods known in the art of nucleoside synthesis, and optionally thereafter forming appropriate organic or phosphate esters, and salts of the latter, by techniques known in the art.

As used herein in relation to the precursor of method (a) the term "4-(substituted)-1-β-D-ribofuranosyl-prazolo[3,4-d]pyrimidine derivative" includes such organic and phosphate esters, and salts of the latter, as are appropriate to the final product of the process.

In method (a) (i) the halogen atom may be a chlorine, bromine or iodine atom. The base used in this method may be an alkali or alkaline earth metal hydroxide or alkoxide, quaternary ammonium hydroxide hydrogen carbonate or carbonate, or a basic resin such as Dowex 1-X8 (bicarbonate) (Dowex is a Registered Trade Mark) supplied by Bio-Rad Laboratories, California, U.S.A. The solvent may be water, a lower alcohol, such as methanol or ethanol or an aprotic solvent such as N,N-dimethylsulphoxide or hexamethylphosphoric triamide, although N,N-dimethylformamide is preferred.

When method (a) (ii) is employed, it is desirable to protect the hydroxyl groups of the ribosyl moiety of the precursor with blocking groups, that is with acyl groups, provided by the use of such acylating agents as acid anhydrides, e.g. acetic anhydride, or acid chlorides, e.g. benzoylchloride. These blocking groups may subsequently be removed by conventional methods of deacylation such as treatment with alcoholic ammonia or an alkali metal alkoxide followed by neutralisation of the base.

Method (a) (ii) may be applied to any suitable 4-halogeno-, 4-alkylthio- or 4-aralkylthio- substituted precursor and can thus be used to interconvert compounds of formula (I) by nucleophilic displacement of the 4-substituent. The radical X may conveniently be a sodium or potassium mercaptide, however other metal mercaptides are also suitable. In this particular method it is preferred that the 4-substituent of the precursor is a halogen atom or a lower alkylthio group, especially a methylthio group.

Chemical processes may be employed in method (b), using a compound of formula (II) in which Q is a hydrogen or a metal atom, e.g. an alkali metal atom such as sodium or other leaving group, and the riboside donor system comprises a reactive ribose derivative such as a 1chlororibose derivative, the reaction being performed in an appropriate solvent system such as an aprotic solvent, e.g. dimethyl formamide or acetonitrile. However, it is preferred that enzymatic or microbiological processes are used.

Such enzymatic processes include the preparation of compounds of formula (I) from the appropriate free base using phosphorylase type enzymes in a manner known in the art: see for instance T. A. Krenitsky, G. B. Elion, R. A. Strelitz, G. H. Hitchings, *J.Biol.Chem.*, 242,2675–2682 (1967); U.K. Patent Application No. 45668/77 cf European Patent Application No. 78 101 295.0 in which case, Q is hydrogen and the riboside donor system consists of appropriate purine and/or pyrimidine-1-B-D ribosides and/or ribose-1-phosphate and the appropriate enzyme or enzymes.

Alternatively the ribosidation may be accomplished by microbiological processes such as that disclosed in German Offenlegungsschrift No. 2 209 078 wherein Q is hydrogen and the riboside donor system comprises bacteria of the genera Brevibacterium, Arthrobacter, Corynebacterium or Micrococcus and the culture medium which includes glucose.

Whenever the compound of formula (I) is required to carry acyloxy groups for $R^1$, $R^2$, and $R^3$, a corresponding starting compound having hydroxy groups in these positions is reacted with acylating agents such as acetic anhydride or benzoyl chloride according to conventional methods. Acylation may be effected before or after other synthetic steps except that when enzymatic or microbiological processes are to be used for the ribosidation of a compound of formula (II) the acylation must be performed after the ribosidation.

When $R^3$ of the desired compound of formula (I) is to be a phosphate group, this may be introduced into the corresponding compound having a hydroxyl group in that position by phosphorylation using traditional phosphorylating agents such as trialkyl phosphates, e.g. triethyl phosphate, with a phosphorus oxyhalide such as phosphoryl chloride. When this technique is used it is advantageous to block the 2' and 3' positions of the ribose moiety either by blocking only these two positions by using appropriate conditions or by blocking the 2',3' and 5' positions and then selectively deblocking the 5' position. The latter course may be facilitated by first blocking the 5' position with a bulky group, such as a trityl group or a t-butyldimethylsilyl group, then blocking the 2' and 3' positions by conventional means, and finally deblocking the 5' position. After phosphorylation the 2' and 3' positions are then deblocked to afford the required compound.

Rather than block the 2' and 3' positions as described above, it is preferred to use phosphoryl chloride in the presence of a trialklphosphate (preferably triethyl phosphate) and a trace of water at a temperature of about 0° C. or below. This forms the 5'-phosphoro dichloridate which is then hydrolysed to the 5'-phosphate upon treatment with water at slightly basic pH.

Salts of phosphate-substituted compounds of formula (I) are obtained by conventional reactions between the phosphate derivative and an appropriate base in aqueous media.

The precursors for use in method (a) may be well known compounds such as 4-hydroxy-, 4-thio or 4-methylthio-1-β-D-ribofuranosylphyrazolo[3,4-d]pyrimidine derivatives, or may be obtained therefrom by conventional techniques. These ribosides may have been prepared from the corresponding free pyrazolo[3,4-d]pyrimidine bases by ribosidation as described for method (b) above.

The 4-halogeno precursor can be derived by treating an acylated derivative of 4-hydroxy-pyrazolo[3,4-d]pyrimidine riboside with a phosphoryl halide, the corresponding Villsmeier reagent or other known halogenating reagents. Alternatively, treatment of the 4-thio analogue with chlorine or bromine and the appropriate hydrogen halide in a lower alcohol at low temperature, affords the 4-halogeno precursor.

The 4-thio substituted precursor may be obtained from the acylated 4-halogeno-pyrazolo[3,4-d]pyrimidine riboside by treatment of the latter with thiourea or sodium hydrosulphide.

The 4-alkylthio- and 4-aralkythio substituted precursors may be derived from other compounds of this class, from the 4-halogeno precursor or from the 4-thio precursor by process (a), mutatis mutandis. Compounds of formula (II) for use in method (b), i.e. the 1-unsubstituted analogues of compounds (I), may be produced by the techniques described above for the production of precursors and by method (a) above, mutatis mutandis.

Simple reagents of the formula $R(CH_2)_n X$ for use in method (a) above or for producing compounds of formula (II) for use in method (b) may be available commercially (e.g. from Aldrich Chemical Co., Milwaukee, Wisconsin, U.S.A.). However all these reagents, $R(CH_2)_n X$ may be produced by methods well known in the art. Those reagents wherein R is a phenoxy, phenylthio, alkoxy or alkylthio group are produced by the following methods from either the appropriate w-halogenoalkyl alcohol or a,w-dihalogeno alkane.

The w-halogenated alcohols are generated by reduction of the corresponding w-halogenoalkyl carboxylic acid, chloride or ester using reducing agents such as lithium aluminium hydride or sodium borohydride or by catalytic hydrogenation using a catalyst such as platinum oxide. The w-halogenoalkyl alcohol is then reacted with the alkoxide, phenoxide, thiolate or phenylthiolate corresponding to the R moiety, (which is generated by the action of an alkali metal or its hydride, carbonate or methoxide, on the appropriate alcohol or thio) in an aprotic solvent such as N,N-dimethylformamide, diglyme, ether or dimethylsulphoxide or in the alcohol or thiol corresponding to R, at a temperature between 20° C. and 150° C., preferably up to 100° C. The w-hydroxyether or w-hydroxythioether so formed is then halogenated by methods known in the art to afford the required reagent $R(CH_2)_nX$.

Alternatively an a,w-dihalogenated alkane is added, in greater than three fold excess, to a solution of the metal alcoholate or thiolate (as described above) in an aprotic solvent such as N,N-dimethylformamide, diglyme, ether or dimethylsulphoxide or in the alcohol or thiol corresponding to R and the reaction is allowed to proceed, at a temperature of 20° C. to 150° C. preferably up to 100° C., until the solution is no longer basic. The w-halogenated ether or thioether of formula $R(CH_2)_nX$ may then be used to produce compounds of formula (I) or (II).

In a third aspect of the present invention there is provided a 1-β-D-ribofuranosylpyrazolo[3,4-d]pyrimidine derivative of general formula (III).

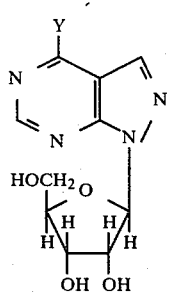

(III)

wherein Y is a halogen atom,

In a fourth aspect of the present invention there is provided a compound of general formula (IV)

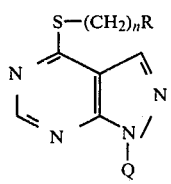

(IV)

wherein n, R and Q are as hereinbefore defined.

Compounds of formula (I) as hereinbefore defined are useful for treating coccidial infections, or preventing them, in livestock. The compounds may be administered alone, or in association with carriers.

In a further aspect of the present invention there is provided a pharmaceutical formulation comprising at least a compound of formula (I) for administration to livestock.

It may be convenient to administer the compounds in association with various carriers and additives to facilitate that administration. In particular, the compounds may be administered in the foodstuff or drinking water provided for the livestock.

The present invention, in a further aspect, therefore provides a pharmaceutical composition comprising a compound of formula (I) in association with a carrier therefor.

Carriers are materials which are useful for the purpose of administering the compound while being otherwise inert as regards interaction with the compound and non-toxic to the recipient of the composition. It is particularly preferred that the carrier is the foodstuff or drinking water provided for the livestock.

When incorporated into foodstuff or drinking water the compounds may be administered at a concentration of about 10 ppm to 400 ppm, preferably 50 ppm to 200 ppm and most preferably 100 ppm.

Some compounds of formula (I) are insufficiently soluble for administration in drinking water. In this case the phosphate ester, or more preferably, a salt thereof can be employed.

In a further aspect of the present invention there is provided a method for preventing or treating coccidial infections of livestock comprising the administration of an effective anticoccidial amount of a compound of formula (I) or a formulation or composition thereof.

The invention will now be illustrated by the following Examples, which should not be construed as limiting the invention in any way.

EXAMPLE 1

Preparation of 4-(2-phenylethylthio)-1-B-D-ribofuranosyl-pyrazolo(3,4-d) pyrimidine Dowex (Registered Trade Mark) 1-X8 (bicarbonate) (4.0g) was mixed with 4-mercapto-1-B-D-ribofuranosylpyrazolo(3,4-d)pyrimidine (2.0g) and methanol was added. The mixture was warmed and stirred until no ultra-violet absorbing material remained in solution. 2-Phenylethyl bromide (1.3g) was added and the mixture stirred at ambient temperature for 3 days. The resin was removed by vacuum filtration and washed with methanol. The filtrate and washings were combined and the methanol evaporated in vacuo to afford after trituation with warm diethyl ether a solid, 4-(2-phenylethylthio)-1-B-D ribofuranosylpyrazolo (3,4-d)pyrimidine m.p. 85-87° C.

EXAMPLE 2

Preparation of 4-(3-phyenylpropythio)-1-B-D-ribofuranosylpyrozolo-(3,4-d)pyrimidine By a method exactly analogous to that of Example 1 the title compound, (mp 95-97° C.) was prepared.

EXAMPLE 3

Preparation of 4-(3-(4-methylphenyl)-propylthio)-1-B-D-ribofuranosylpyrazolo(3,4-d)pyrimidine 4-Mercapto-1-B-D-ribofuranosylpyrazolo(3,4-d)pyrimidine (2 g) was added to ethanol (0.1l) containing aqueous sodium bicarbonate (0.6 g/ml). 3-(4-methylphenyl)-propyl chloride (1.19 g) in ethanol (0.005 l) was added dropwise with stirring. The mixture was warmed on a steam bath to effect solution then heated under reflux for 24 hours. The reaction mixture was evaporated to a syrup (in vacuo) which was triturated with hexane and warm petroleum ether to afford a syrup. The syrup was heated with water, cooled and the solid isolated. The solid was recrystalized twice from ethanol to give 4-(3-(4-methylphenyl)-propylthio)-1-B-D-ribofuranosylpyrazolo(3,4-d) pyrimidine (m.p 118°–120.5° C.) as the hemihydrate.

EXAMPLE 4

By a method exactly analogous to that of Example 3, the following were prepared.

| Example | Halide | duration (hours) | product (1-B-D-ribe-furanoayl-pyrazolo(3,4-d)-pyrimidine | M.pt (°C.) |
|---|---|---|---|---|
| 4a | Cl | 41 | 4-(3-(4-chloro-phenyl)-propyl-thio)- | 129.5–130.5 |
| 4b | Cl | 48 | 4-(2-(4-choro-phenyl)-ethyl-thio)- | 103–105 (soften 100) |

EXAMPLE 5

Preparation of 4-(2-phenoxyethylthio)-1-B-D-ribofuranosyl-prazolo(3,4-d)pyrimidine Crude 2-phenoxyethyl chloride (2.7 g) was added to a stirred solution of 4-mercapto-1-B-D-ribofuranosyl-pyrazolo(3,4-d)pyrimidine (2.0 g) and potassium carbonate (1.07 g) in N,N-dimethylformamide. The solution was heated (40° C. on an oil bath) for 24 hours. After cooling the reaction mixture was poured into water (0.20 l) and the resultant precipitate was collected.

The 4-(2-phenoxyethylthio)-1-B-D-ribofuranosyl-pyrazolo(3,4-d)pyrimidine so obtained was recystallised from methanol, m.p. 125°–126° C.

EXAMPLES 6 AND 7

The compounds of Examples 6 and 7 wree prepared by a method exactly analogous to that of Example 5 except that the reaction was conducted for the duration shown.

| Example | Halide | Duration (hours) | Product (1-B-D-ribo-furanosyl-pyrazolo-(3,4-d)pyrimidine | m.p. (°C.) |
|---|---|---|---|---|
| 6 | Cl | 24 | 4-(2-(4-methylphenyl)-ethylthio)- | 96–97 |
| 7(a) | Cl | 24 | 4-(2-(3-methylphenyl) ethylthio)- | 88–91 |
| 7(b) | Cl | 3 | 4-(4-benzyloxybenzyl-thio)- | 181–185 |
| 7(c) | Cl | 1 | 4-(3-phenyl-2-propynylthio)- | 137 (softens 134) |

EXAMPLES 8 TO 10

The compounds of Example 8 to 10 were prepared using a method exactly analogous to that used in Example 3

| Example | Product (-1-β-D-ribofuranoxyl pyrazolo(3,4-d)pyrimidine | m.p. (°C.) |
|---|---|---|
| 8 | 4-(4-methylbenzylthio)- | 125–127 |
| 9 | 4-(4-chlorobenzylthio)- | 114–117 (soften 80) |
| 10 | 4-(3-chlorobenzylthio)- | 90 (soften 75) |

EXAMPLE 11

Preparation of 4-(5-phenylpentylthio)-1-β-D-ribofuranosyl-pyrazolo[3,4-d]pyrimidine Crude 5-phenylpentyl chloride (1.3 g) was added to a stirred solution of 4-mercapto-1-β-D-ribofuranosyl-pyrazolo [3,4-d]pyrimidine (2.0 g) and potassium bicarbonate (0.7 g) in N,N-dimethylformamide. The reaction mixture was heated on a steam bath for 25 hours. An additional 0.7 g of potassium bicarbonate was added and after heating for 1 hour more, the mixture was poured into water. The cooled aqueous mixture was extracted with chloroform. The chloroform soluble material was chromatographed on a silica gel column. The fractions containing the compound were combined and evaporated. Trituration with ether gave 0.4 g of crude product. This was dissolved in ethyl acetate and washed with water. The dried ethyl acetate solution was evaporated and purified by reversed phase chromatography in methanol water (80:20 vol/vol) to give 0.28 g of product m.p. 72°–75° C. (indefinite).

Analysis Calc'd for $C_{21}H_{26}N_4O_4S$: Theory: C: 58.58% H: 6.09% N: 13.01% S: 7.45%; Found: C: 58.83% H: 6.15% N: 13.06% S: 7.57%.

EXAMPLE 12

In order to assess the activity of compounds of formula (I) against coccidia, the compounds were administered to groups of 5 male Ross Ranger chicks (7 days old), at various dosages in the diet, for 6 days. The chicks were each infected with Eimeria tenella and E. acervulina one day after the beginning of the medication. The compounds had some effect on the E. acervulina and cleared chicks of E. teneila as indicated in Table 1 below. No obvious signs of toxicity were observed during this experiment.

TABLE I

Number of chicks cleared of E. tenella by administration of compounds of formula (I) at various dose levels.

| Compound of Example No. | Doses level (ppm of diet) | | | |
|---|---|---|---|---|
| | 200 | 100 | 50 | 25 |
| 1 | 5 | 1 | 1 | 1 |
| 2 | 5 | 5 | 4 | 1 |
| 3 | 1 | NT | NT | NT |
| 4[a] | 5 | NT | 0 | 1 |
| 4[b] | 1 | NT | NT | NT |
| 5 | 2 | NT | NT | NT |
| 6 | 2 | NT | NT | NT |
| 7[a] | NT | 1 | NT | NT |
| 7[b] | 5 | 5 | 5 | 3 |
| 7[c] | 5 | 2 | 0 | 1 |
| 8 | 5 | 5 | 4 | 2 |
| 9 | 5 | 5 | 4 | 3 |
| 10 | 1 | NT | NT | NT |
| 11 | NT | 2 | NT | NT |

We claim:
1. A compound of formula (I)

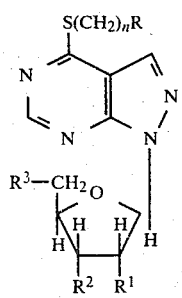

wherein n is an integer of 1 to 6 and R is lower alkoxy or lower alkythio group or phenoxy or phenylthio group or an unsubstituted or mono-substituted phenyl group, or, when n has the value 1, a group —C≡-C—R⁵, wherein R⁵ is a mono- di- or tri-substituted phenyl or an unsubstituted phenyl, substituents for the aforementioned phenyl groups being selected from halogen atoms and lower alkyl, lower alkoxy, trifluoromethyl, benzyloxy, phenoxy, amino, mono- or di-lower alkylamino, and hydroxyl, and either R¹, R² and R³ are the same and are hydroxyl or acyloxy groups —O—CO—R⁴ wherein R⁴ is a hydrogen atom or a lower alkyl group or a substituted or unsubstituted phenyl group wherein the substituents are selected from the group consisting of amino, hydroxyl, nitro, lower alkyl, lower alkoxy or halogen or R¹ and R² are hydroxyl or acyloxy groups as hereinbefore defined and R³ is a phosphate group, or a salt thereof.

2. A compound according to claim 1 wherein R¹ and R² are hydroxyl and R³ is hydroxyl or a phosphate group or a salt thereof.

3. A compound according to claim 1 wherein n has a value from 1 to 3 and R is a substituted or unsubstituted phenyl group.

4. A compound according to claim 3 wherein R is a substituted phenyl group, the substituents being selected from the group consisting of halogen and lower alkyl.

5. A compound of formula (III).

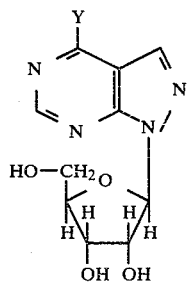

(III)

wherein Y is a halogen atom.

6. A compound of general formula (IV)

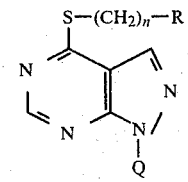

wherein n, is an integer of 1 to 6, R is lower alkoxy, lower alkylthio, phenoxy, phenylthio, phenyl or mono-substituted phenyl, or when n is 1, a group —C≡C-R⁵, wherein R⁵ is mono-, di or tri-substituted phenyl, substituents for the aforementioned phenyl being selected from the group consisting of halogen, lower alkyl, lower alkoxy, trifluoromethyl, benzyloxy, phenoxy, amino, mono- or di-lower alkylamino and hydroxyl groups and Q is hydrogen or an alkali metal atom.

7. A compound or salt of claim 1 which is 4-(2-phenylethylthio)-1-β-D-ribofuranosylpyrazolo-(3,4-d)pyrimidine or a pharmaceutically acceptable salt thereof.

8. A compound or salt of claim 1 which is 4-(3-phenylpropylthio)-1-β-D-ribofuranosylpyrazolo-(3,4-d)pyrimidine or a pharmaceutically acceptable salt thereof.

9. A compound or salt of claim 1 which is 4-(3-(4-methylphenyl)propylthio)-1-β-D-ribofunanosyl-pyrazolo(3,4-d)pyrimidine (3,4-d)pyrimidine or a pharmaceutically acceptable salt thereof.

10. A compound or salt of claim 1 which is 4-(4-benzyloxybenzylthio)-1-β-D-ribofuranosylpyrazolo(3,4-d)pyrimidine or a pharmaceutically acceptable salt thereof.

11. A compound or salt of claim 1 which is 4-(4-methylbenzylthio)-1-β-D ribofuranosylpyrazolo(3,4-d)pyrimidine or a pharmaceutically acceptable salt thereof.

12. A compound or salt of claim 1 which is 4-(4-chlorobenzylthio)-1-β-D ribofuranosylpyrazolo(3,4-d)pyrimidine or a pharmaceutically acceptable salt thereof.

13. A pharmaceutical composition for use in combatting coccidiosis comprising an effective coccidiosis combatting amount of a composition or salt of claims 1, 7, 8, 9, 10, 11 or 12 in association with a carrier therefor.

14. A method for combatting coccidial infections of livestock comprising the administration to the livestock of an effective, non-toxic coccidiosis combatting amount of the compound or salt of claims 1, 7, 8, 9, 10, 11 or 12.

15. A method for combatting coccidial infections of livestock comprising the administration to the livestock of an effective, non-toxic coccidiosis combatting amount of the compound or salt of claims 1, 7, 8, 9, 10, 11 or 12 in foodstuff or drinking water in a concentration of from about 25 ppm to 400 ppm.

* * * * *